United States Patent [19]
Lund et al.

[11] 3,972,966
[45] Aug. 3, 1976

[54] APPARATUS FOR PRODUCING PULSED LIQUID FLOW IN A DISTILLATION COLUMN

[75] Inventors: Terry E. Lund, Downers Grove; Robert F. Millar, McCook, both of Ill.

[73] Assignee: Universal Oil Products Company, Des Plaines, Ill.

[22] Filed: Jan. 21, 1975

[21] Appl. No.: 542,872

[52] U.S. Cl. ............................ 261/114 R; 137/138; 137/139; 202/158; 261/114 A
[51] Int. Cl.² ............................................. B01F 3/04
[58] Field of Search ..... 261/114 R, 114 A, 114 VT, 261/114 JP, 114 TC, 110, 97; 202/158; 137/132, 136–139, 142, 143

[56] References Cited
UNITED STATES PATENTS

| 760,770 | 5/1904 | Adams | 137/138 X |
| 871,427 | 11/1907 | Miller | 137/139 |
| 1,862,758 | 6/1932 | Merley | 261/114 R |
| 2,385,355 | 9/1945 | Gerhold | 261/114 R X |
| 2,394,679 | 2/1946 | Gerhold | 261/114 R |
| 2,416,724 | 3/1947 | Whaley | 261/114 R |
| 2,501,114 | 3/1950 | Whaley, Jr. | 261/114 R X |
| 2,707,163 | 4/1955 | Thibaut | 261/114 R X |
| 2,776,820 | 1/1957 | Bond, Jr. | 261/110 X |
| 2,902,413 | 9/1959 | Kassel et al. | 261/114 R X |

FOREIGN PATENTS OR APPLICATIONS

| 877,018 | 9/1961 | United Kingdom | 261/114 R |

Primary Examiner—Tim R. Miles
Assistant Examiner—Richard L. Chiesa
Attorney, Agent, or Firm—James R. Hoatson, Jr.; Robert W. Erickson; William H. Page, II

[57] ABSTRACT

Apparatus for pulsing the flow of the liquid between the trays of a distillation column with only a small change in liquid level. In the preferred embodiment, a dome-like capping plate is mounted over the upper end of a downcomer conduit and overlaps the portion of the downcomer which extends above the fractionation tray as a weir to form a sealed liquid passageway having the shape of an inverted U. A siphon which starts when liquid is pushed over the top of the weir is broken when the liquid level on the tray falls to the lower end of a U-shaped conduit communicating with the upper volume of the capping plate.

2 Claims, 4 Drawing Figures

U.S. Patent  Aug. 3, 1976  3,972,966
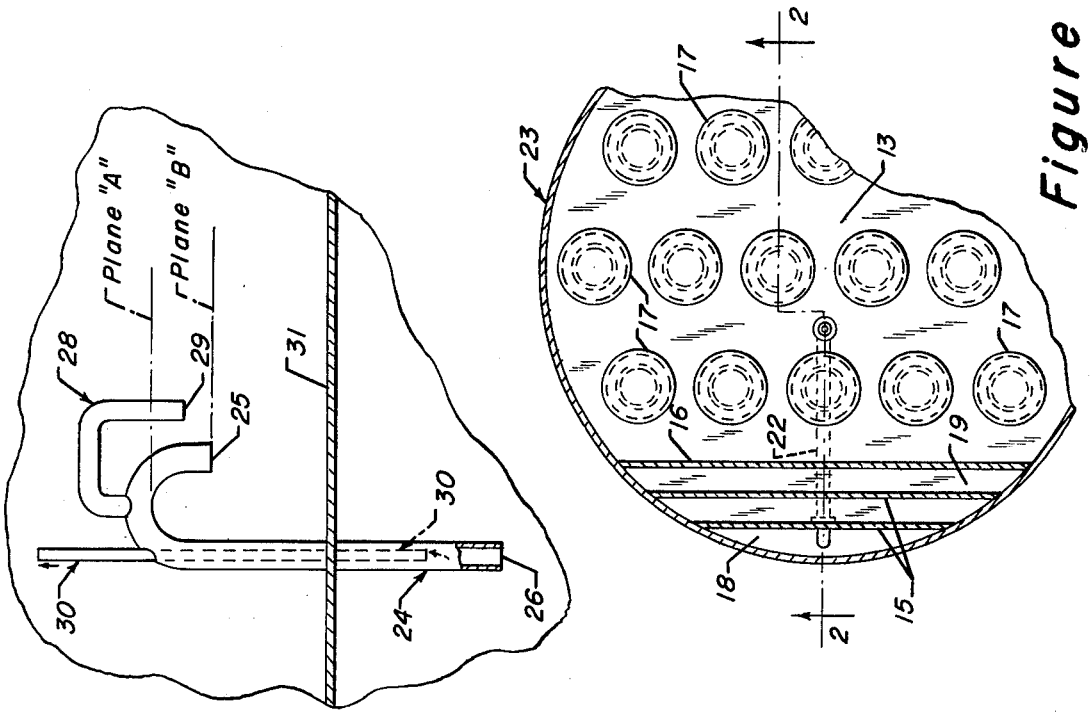
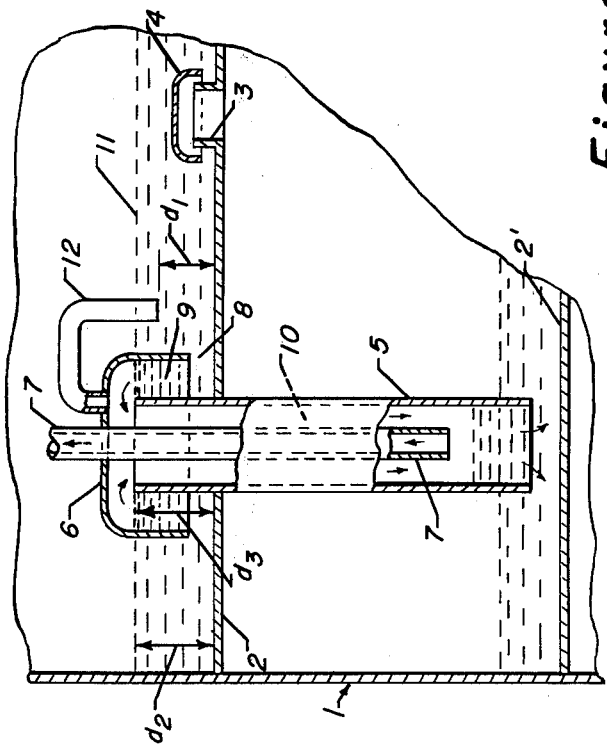
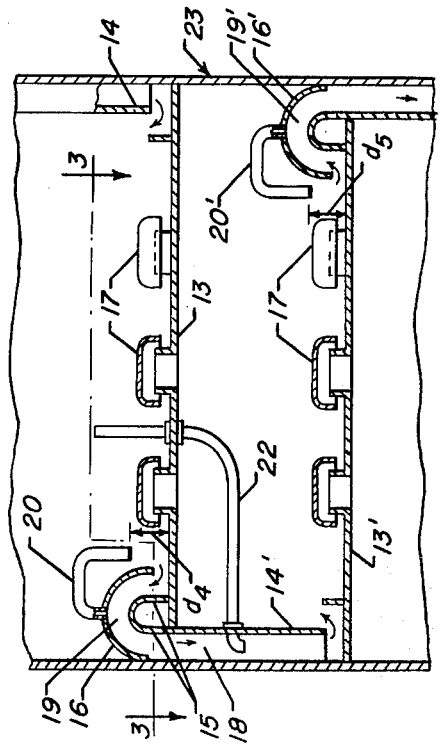

APPARATUS FOR PRODUCING PULSED LIQUID FLOW IN A DISTILLATION COLUMN

FIELD OF THE INVENTION

The invention relates generally to the design of distillation apparatus, including trays and downcomers. It also relates to the design of an apparatus which produces a pulsed liquid flow using an intermittent siphon action. The invention relates specifically to a capped or curved downcomer having a liquid flow path in the shape of an inverted U above the surface of the tray from which it removes liquid and a siphon-breaking conduit communicating with this part of the liquid flow path.

PRIOR ART

The use and design of fractionation trays is well known to those skilled in the art. It is known that the efficiency of a tray is affected by liquid from the tray above backmixing with the liquid on a tray. This is discussed on pages 18–19 and 18–20 of the fourth Edition of *Perry's Chemical Engineer's Handbook*. However, the effect of pulsed liquid flow or means for producing it are not discussed therein. The benefits which are derived by a periodic pulsing of the liquid held on a fractionation tray are the subject of a mathematical analysis presented in a series of papers published in *Industrial and Engineering Chemistry, Process Design and Development*, in Volume 6, No. 1 for January, 1967 at Page 30 and in Volume 7, No. 1 for January, 1968 at Page 61. No discussion of suitable apparatus for producing the pulsation is contained in these references.

Various designs for weirs and downcomers are known in the art, with examples being presented in U.S. Pat. Nos. 2,385,355 (Cl. 261–110) and 3,700,216 (Cl. 261–114). A downcomer having a U-shaped upper portion is shown in FIG. 11 of U.S. Pat. No. 2,707,163 (Cl. 196–49). This design is used to remove heavier material from the bottom of the liquid inventory on the tray. However, this reference specifies the use of a perforation at the top of the U-shaped portion to prevent a siphon action.

BRIEF SUMMARY OF THE INVENTION

The invention provides fractionation trays of increased efficiency by providing a pulsed flow of liquid without the use of moving parts or control systems. The pulses are generated with only a minimal change in the liquid level on the tray through the use of two interconnected conduits having U-shaped portions. An imperforate capping plate is preferably placed over the raised upper end of a downcomer conduit which forms a weir on the surface of the fractionation tray. The capping plate extends downward below the upper edge of the weir at a point outside of the weir to create a U-shaped liquid transfer conduit having legs of unequal length. A curved siphon-breaking conduit communicates with the volume within the capping plate, rises above the capping plate and then descends below the top of the U-shaped liquid-transfer conduit. When the liquid inventory on the tray becomes sufficient to cause liquid to flow under the capping plate and up over the weir a siphon starts and is in turn broken when the liquid level reaches the end of the siphon-breaking conduit.

DESCRIPTION OF THE DRAWING

FIG. 1 shows a vertical cross-section of a portion of a fractionation tray constructed according to the preferred embodiment of the invention.

FIG. 2 shows a vertical cross-section of a portion of a distillation column using an alternative downcomer conduit construction.

FIG. 3 is a horizontal cross-section taken above tray 13 of FIG. 2.

FIG. 4 illustrates the construction of a downcomer with a unitary liquid transfer conduit.

In FIG. 1, wall 1 represents the cylindrical outer wall of a distillation column. There is shown a first fractionation tray 2 and a second fractionation tray 2' located below it. A bubble cap vapor-liquid contacting means comprising a vapor passageway surrounded by a weir 3 and covered by a cap 4 represents the plurality of such devices used on the tray. There is also shown the liquid inventory of the tray having a total height of $d_2$ at the upper liquid surface 11. As illustrated, in the preferred embodiment a downcomer is formed from a cylindrical liquid transfer conduit 5 which extends upward above the upper surface of the fractionation tray 2 to form a cylindrical weir. This weir has a height represented by $d_3$. Covering the upper open end of the conduit is a dome-like capping plate 6, which has a shape similar to that of cap 4. The capping plate 6 overlaps the weir and extends downward below the upper edge of the weir to within a small distance from the upper surface of the fractionation tray 2. This construction forms a horizontal liquid passageway 8 between the bottom of the capping plate 6 and the upper surface of the fractionation tray 2 and also forms a vertical annular liquid passageway 9 between the weir and the capping plate. A U-shaped siphon-breaking conduit 12 openly communicates with the volume within the top of the capping plate 6, rises above the capping plate and then descends to the minimum desired liquid level indicated by $d_1$. A vapor venting conduit 7 passes through the top of the capping plate 6 and extends downward within the downcomer conduit 5. The upper end of this venting conduit is located above the maximum normal liquid level attainable on the tray. When the liquid level $d_2$ reaches a height sufficient to push liquid under the capping plate and over the top of the weir, a liquid stream begins to flow downward through the annular space 10 between the outer surface of the vapor venting conduit 7 and the inner surface of conduit 5. Vapor venting conduit 7 allows trapped vapor within the conduit 5 to escape. A siphon is formed which rapidly draws the liquid inventory of tray 2 downward through the conduit and onto tray 2'. When the liquid level 11 reaches level $d_1$ at the lower edge of the siphon-breaking conduit 12, the siphon is broken and the liquid stream no longer flows through the downcomer.

In FIG. 2, the vertical portion of the liquid-transfer conduit is formed by slicing a chord off of one edge of an upper fractionation tray 13 and placing a vertical wall 14' on the edge of this chord. This forms the narrow elongated space 18 which is also shown in FIG. 3. This part of the downcomer conduit is therefore formed by the inner wall of a distillation column 23 and the vertical wall 14'. The vertical wall 14' extends upward above the upper surface of the fractionation tray 13 and then bends downward in an inverted U-shaped portion 15. This U-shaped portion is the weir of this embodiment. The imperforate capping plate 16 also has the shape of an inverted U and overlaps the wall 15 to form the U-shaped liquid passageway 19. The capping plate 16 extends downward below the upper edge of the U-shaped section 15. A vapor conduit 20 communicates with the liquid passageway 19 through an opening in the capping plate 16. The conduit then extends downward to a minimum desired liquid level $d_4$. A similar downcomer formed by wall 14 is shown on the right-hand side of the Figure. Liquid from above overflows a weir and descends through this conduit between the inner surface of the distillation column 23 and the vertical wall 14. Hydrocarbon vapors pass through the bubble caps 17 to contact the liquid inventory contained on the tray 13. The vapor venting conduit 22 communicates with the internal volume of the downcomer conduit and then passes through wall 14' and through fractionation tray 13 to allow vapors to exit from the downcomer conduit and pass into the volume located above the liquid on tray 13. A capping plate 16' forms a second U-shaped liquid passageway 19' on the lower fractionation tray 13'. A second vapor conduit 20' communicates with the upper portion of the internal volume of the liquid passageway and descends to level $d_5$. Level $d_4$ is closer to the surface of the tray than level $d_5$.

FIG. 3 is presented to give a better understanding of the construction of the apparatus depicted in FIG. 2. It is a horizontal cross-section taken at a point just above the bubble caps 17 and then cutting through U-shaped wall 15 and the capping plate 16. Therefore, it shows the outer wall of the distillation column 23 and the upper surface of the upper fractionation tray 13. Bubble caps 17 are distributed over the vapor-liquid contacting area of the fractionation tray to provide uniform and thorough contacting of the rising vapors with the liquid contained upon the tray. The elongated horizontal shape of the internal volume 18 of the liquid-transfer conduit is more clearly seen in this view. U-shaped wall 15 is cut across at two points indicated by the two walls adjacent to the inner edge of the downcomer conduit. A vertical liquid passageway 19 begins at the point between the inner wall 15 and the bottom edge of the vertical portion of the capping plate 16. The vapor venting conduit 22 extends from within the internal volume 18 of the downcomer to a point above tray 13.

In FIG. 4, a single unitary tube is used to form the liquid-transfer conduit 24 of the downcomer. The upper portion of the conduit is bent in the shape of an inverted U, the horizontal section of which divides the conduit into a shorter leg having an open end 25 and a longer leg having an open end 26. The longer leg passes through the surface of a fractionation tray 31 to a lower tray. A curved siphon-breaking conduit 28 having the shape of an inverted U is attached to the central base of the liquid-transfer conduit to form an enclosed vapor flow path from the opening 29 to the enclosed liquid flow path within conduit 24. The elevation of opening 29 must be between plane A and plane B. A vapor venting conduit 30 extends vertically downward through the top surface of the conduit 24 to a point below the open end 25 of conduit 24.

DETAILED DESCRIPTION

The distillation of mixtures of various hydrocarbons and inorganic liquids is performed in a great many industrial processes as a method of separating the mixtures into their individual components. This has prompted great efforts to reduce both the capital costs of constructing distillation apparatus and the utility costs of operating them. One of the main areas of attention has been the relative efficiency of the various types of trays or other vapor-liquid contacting means used within the apparatus, such as comparisons between sieve and bubble cap trays. Operational variables affecting the performance of these columns have also been investigated. In the previously cited article on page 30 of *I & EC Process Design and Development*, Volume 6, No. 1, January, 1967, a mathematical analysis is presented of the improved operational efficiency of a periodically operated column as compared to a conventional column. In this method of operation a fraction of the liquid holdup of each stage is periodically moved to the stage below and mixed there with a corresponding remaining fraction of the liquid holdup of that tray. This assumes the absence of the continuous backmixing of the contents of the lower tray with the liquid descending from the upper tray as occurs in a conventional column. The flow rate of the vapor phase upward is constant. It is the objective of this invention to provide a means to achieve this periodic transfer of the liquid phase contained within a distillation column and thereby provide a distillation method of increased efficiency. Pulsing operations may be classified into one of two modes. In the first, the incoming pulse does not start until the receiving tray has been partially emptied, and there is a relatively large fluctuation in liquid level. In the other mode of operation, the level on the tray is not subject to major changes, and liquid forming the pulses simultaneously enters and departs the tray. It is the further objective of the invention to provide an apparatus for practicing the latter mode of a pulsing operation.

The invention provides a design for fractionation trays and downcomers which creates a pulsed flow of liquid without requiring the use of moving parts or control systems. This simplicity is a great advantage in that the method of the invention therefore does not require calibration or maintenance. The system will also prove very dependable for this same reason. A distillation column using the invention requires very little additional capital costs in comparison to placing an automated flow control system in the downcomers of a continuous liquid flow column. The invention also has the advantage of allowing the variation of the magnitude of the pulses while the column is operating without any structural changes. This allows an onstream optimization of the pulsing operation to be performed. The U-shaped upper portion of the liquid transfer conduit also prevents the undesirable passage of foam into the downcomer. Finally, use of the second mode of operation decreases disturbances in the column's operation due to changing liquid loadings and increases a column's capacity compared to the first mode of operation.

In a typical fractionation tray, a weir is often placed around the upper open end of a downcomer to maintain a desired liquid inventory upon the upper surface of the fractionation tray. Excess liquid material spills over this weir at a fairly constant rate. In practicing the preferred embodiment of the invention, a dome-like capping plate is placed over the weir formed by the raised upper end of a cylindrical downcomer and extended downward below the upper edge of the weir at a first predetermined distance outward from the weir. This capping plate stops a second predetermined distance from the upper surface of the fractionation tray to leave an unobstructed liquid flow path between the bottom edge of the capping plate and the tray. This opening in the preferred embodiment has the shape of a vertically orientated cylinder which is concentric with the weir. This cylinder has a height equal to the second preselected distance and provides an available liquid flow path which has a minimum cross-sectional area greater than that available within the downcomer, as hereinafter described. The larger diameter of the capping plate as compared to the weir results in the formation of an annulus which forms a continuation of the liquid flow path. The minimum available cross-sectional area of the resulting ring-shaped liquid flow path located between the outer surface of the weir and the inner surface of the capping plate should also be greater than that available within the downcomer. The upper, inner surface of the capping plate is raised above the top edge of the weir to allow a liquid flow path into the downcomer which also has this minimum reference area. In summary, the dome-like capping plate fits over the weir at the top of the downcomer so to provide a U-shaped liquid flow path which extends under the edge of the capping plate, up between the capping plate and the weir and then over the weir and into the downcomer and which has an area available for liquid flow greater than the minimum available in the downcomer. Each flow path should have a greater available cross-sectional area than the next one downstream on the same tray.

The preferred embodiment also comprises a curved siphon-breaking vapor conduit which preferably has the shape of an inverted U. This conduit preferably communicates with an uppermost portion of the internal volume of the capping plate through a hole in the capping plate and also preferably extends upward above the maximum liquid level which is expected on the tray. This higher elevation prevents the passage of liquid through the conduit, and the conduit will therefore not transfer liquid during the siphon action. The conduit then extends downward to a point below the upper edge of the weir within the capping plate, or below that portion of a liquid flow path which functions in the equivalent manner. This point will control the lowest liquid level in the tray since the siphon will be broken when the liquid level reaches this point. An opening either in the side or at the end of the siphon-breaking conduit may be used. Alternatively, the siphon-breaking conduit may communicate with the liquid flow path through an opening on the side of this flow path and then bend directly downward. The configuration of the siphon-breaking conduit above its lower open end is therefore not critical to successful operation. The siphon-breaking conduit is preferably in open communication with the base or central terminus of the liquid transfer conduit or with its shorter leg to thereby deliver the vapor to the top of the siphon. Communication at a point lower in the longer leg of the conduit may lead only to an aspiration effect being produced.

In operation, a certain minimum level of liquid indicated by $d_1$ of FIG. 1 is always maintained upon the fractionation tray. The level of the liquid on the tray rises above this as more liquid descends from above or condenses from the vapor phase. The liquid surface eventually rises to a critical level indicated by $d_2$. At this point, the hydraulic pressure of the liquid pushes a sizable flow of the liquid through the shorter leg of the conduit and over the top of the weir. The greater available space within the capping plate allows a liquid flow rate which exceeds that within the downcomer, and the top of the downcomer begins to fill with liquid. A liquid seal is then formed in the top of the downcomer. This starts a siphon which pulls liquid downward through the downcomer at a maximum rate set by the minimum available flow path in the longer leg of the downcomer. This siphon action continues to drain the upper plate until the liquid level once again falls to level $d_1$ and vapors pass through the siphon-breaking conduit and into the capping plate. If no liquid enters the tray during the pulse the invention produces pulses which have a magnitude equal to the liquid inventory of the tray between levels $d_1$ and $d_2$. The frequency of these pulses is determined at the rate at which liquid is accumulated on the upper tray. The length of time necessary to transfer the pulse is determined by the maximum flow rate through the downcomer and may be adjusted by varying the minimum available cross-sectional area or the number of the downcomers.

It is preferred that there be only a relatively small change in the level of the liquid retained on the tray. The difference in the elevations of the weir and the bottom of the siphon-breaking conduit should therefore be less than the distance needed to produce a pulse of the desired magnitude. The difference in this elevation should however be sufficient to prevent minor disturbances in the level of the retained liquid from causing liquid to descend through the downcomer. A minor level change will not cause a sufficient flow to initiate a siphon, and unless a critical liquid level is reached, the liquid simply spills over the weir.

When a pulse of liquid from the tray above or from an external pulse-generating means enters a tray, the liquid level rises until the previously described siphon action begins. By providing downcomers of suitable size between contiguous trays, the rates of liquid addition and removal to each tray are equalized. Due to the differing physical properties of the liquids in different parts of the column, the rate of flow of the liquid through the downcomers will not be equal at all points. The rates of flow to and from a single tray will however be very similar when identical downcomers are used. Therefore, the liquid level under normal operating conditions will not rise much above that needed to initiate the siphon. Similarly, the level should not fall to the elevation of the bottom of the siphon-breaking conduit until the addition of pulsed liquid has ceased. The invention therefore provides a means of assuring the sequential transfer of a pulse downward through a column with only a minimum disturbance in the liquid levels. This provides a more uniform gas rate through the trays. A further advantage is that the pulse transmitted through the column is set by the pulse fed to the top tray and is independent of the tray construction. The minimum pulse which may be successfully transmitted is set by the tray inventory between the elevation which starts the siphon and the opening in the siphon-breaking conduit. It is therefore possible to regulate the size of the pulse each tray transmits with a single external controller and to use this controller to optimize the performance of the column. The volume of the pulse transmitted between specific trays is dependent on the liquid/vapor rates which are dependent on the enthalpy balance. Therefore, the pulse volume on the top tray may be vastly different from the bottom tray.

By referring to the Figures, it may be observed that liquid is only removed at a point near the surface of the tray. In contrast, liquid entering the tray flows over a weir and is therefore guided to the top of the retained liquid. Although the liquid on the tray is greatly agitated by the rising vapors, the difference in the density of the incoming liquid may be enough to produce some stratification of the retained liquid. The apparatus will then tend to preferentially remove the original contents of the tray. This effect reduces the backmixing of the liquid and thereby increases the tray efficiency.

To provide a better siphon effect, the downcomer preferably extends downward into liquid retained on the tray below. Therefore, a quantity of vapor is held within the longer leg of the downcomer between the pulses by the liquid seals at the top and bottom of the downcomer. When a pulse starts, this vapor must be either released or pushed out of the bottom of the downcomer. Experiments with transparent columns and downcomers have indicated that this vapor is first subjected to a piston-like compression and then rapidly expelled with a resultant initial delay in the formation of the pulse and a ragged initiation of the desired plug flow of the liquid. These undesired effects are prevented by the provision of a vapor venting conduit which allows the trapped vapors to escape. This is a significant aid which borders on being a necessity. The preferred construction of this tube is a single vertical tube passing through the capping plate and extending downward within the downcomer conduit shown in FIG. 1. It is preferred that the venting conduit extends straight down through the capping plate as shown in FIG. 1 since experiments have indicated there is a tendency to form vapor pockets under any members protruding horizontally into the downcomer conduit. The bottom end of the vapor venting conduit should be located above the liquid level in the bottom of the downcomer conduit. It is preferred that the conduit extends downward a considerable distance since the descending liquid pushes the trapped vapors downward. It must extend downward at least below the top of the weir to allow the formation of a liquid plug flow within the downcomer. The inner diameter of the vapor venting conduit should be the minimum which will still allow a near instantaneous release of the trapped vapors. Increasing the diameter beyond this does not yield any significant benefit and unnecessarily constricts the flow path within the downcomer. The minimum available cross-sectional area of the downcomer in the preferred embodiment is determined by the annulus between vapor venting conduit and the downcomer.

The capping plate and the downcomer conduit are mounted on a liquid support plate which has substantially the same size as the inside of the distillation column. This plate will also contain a large number of vapor transfer means which allow vapors to pass through the tray and into the liquid and which thereby promote mass transfer between these two phases. The preferred embodiment may therefore be described as a fractionation tray which comprises a substantially circular liquid support plate having an upper surface; a plurality of vapor-liquid contacting means located on the liquid support plate; a vertical, cylindrical downcomer conduit having an open upper end and an open lower end and passing through a perforation in the liquid support plate, the downcomer conduit extending upward above the upper surface of the liquid support plate and forming a vertical liquid retaining weir around the perforation in the liquid support plate, the weir terminating at an upper edge located a preselected distance above the liquid support plate, with the downcomer conduit also extending downward below the liquid support plate; an imperforate cylindrical capping plate positioned above and externally overlapping the weir formed by the downcomer to form the upper surface of a volume within the capping plate, with an imperforate portion of the capping plate extending downward below the upper open end of the downcomer and forming an annular vertical liquid passageway between the downcomer and the capping plate having a cross-sectional area greater than the minimum cross-sectional area of the downcomer which is available for liquid flow, the capping plate terminating at a point above the liquid support plate to form a horizontal cylindrical liquid passageway between the capping plate and the liquid support plate having a vertical cross-sectional area at least as great as the minimum available cross-sectional area of the annular, vertical liquid passageway; a vapor venting conduit which passes through the capping plate and has a lower end which communicates with the internal volume of the lower one-half of the liquid transfer conduit and an upper end which is located above the capping plate; and a siphon-breaking conduit which communicates with the volume within the capping plate and extends upward above the capping plate before bending downward to form a U-shaped portion in the conduit, the conduit extending to a lower open end located less than the preselected distance from the upper surface of the liquid support plate.

There are a number of alternative ways in which the invention may be constructed to produce the desired pulsed flow. For instance, the preferred embodiment utilizes the dome-like capping plate previously described, whereas the design shown in FIG. 2 utilizes a U-shaped capping plate overlapping a U-shaped weir along a chordal downcomer. The construction of the weir at the upper open end of the downcomer which passes through the liquid support plate may also vary from the preferred embodiment. The weir may be an independent structure resting on the liquid support plate and not attached to the downcomer conduit. The weir may be chordal, circular or semi-circular but is located between the upper open end of the downcomer and the vapor-liquid contacting area of the liquid support tray. It is also possible to vary the placement and design of the vapor venting conduit as these same; Figures indicate. In principle, the function of the vapor venting conduit is satisfied by placing a perforation in the wall of the downcomer conduit. However, this is not the most desired mode because there is a higher absolute pressure present under the upper fractionation tray than above it. The vapor venting conduit should therefore have its upper end located above the upper fractionation tray.

The desired liquid-transfer conduit of the downcomer may be described in generalized terms as an enclosed vertical liquid flow path, the upper portion of which has the shape of an inverted U. This flow path may be delineated by either the weir and capping plate combinations described above or by a single monolithic conduit. The latter arrangement utilizes a single unitary liquid-transfer conduit which is vertically orientated along its major axis and extends straight upward from the approximate level of the upper surface of a lower second fractionation tray to a first preselected distance above the upper surface of the first fractionation tray and then bends downward to a second preselected distance above the upper surface of the first fractionation tray to form a U-shaped liquid path in the upper one-half of the liquid transfer conduit. The required length of the liquid transfer conduit is set by the tray spacing of the column in which it is used. The middle of the U-shaped portion of the conduit is a horizontal section also referred to herein as its central base. This horizontal section divides the conduit into a shorter vertical leg which contains the liquid inlet at the upper end of the conduit and a longer vertical leg which comprises the lower one-half of the conduit and contains the liquid outlet opening. The length of the respective legs is measured from the horizontal section, which is the uppermost part of the conduit when it is in use. The longer leg should be at least twice as long as the shorter leg, and preferably is four times as long. By the term "unitary", it is intended to refer to a conduit which is defined by a single uniform structure in contradistinction to a conduit which is located in spaces between different elements, such as between the capping plate and weir of FIG. 1. A unitary conduit forms its own weir and capping plate. The liquid-transfer conduit may of course be fabricated from several components. For instance, the conduit may be formed by several lengths of piping joined together. The conduit of FIG. 4 could be formed from a commercially available U and a section of straight pipe.

The liquid-transfer conduit and the siphon-breaking conduits for a unitary liquid-transfer conduit are designed in the same manner as previously described and are preferably unitary conduits. In generalized terms, the siphon-breaking conduit must extend downward below that structure which operates as the weir at the top of the downcomer. In a unitary, tubular conduit this position is equilvalent to the lower inner surface of the conduit in the horizontal section, or base, of the U-shaped portion. The siphon-breaking conduit must extend downward to a point below the horizontal plane at the level of this surface to allow proper placement of the vapor opening. To successfully limit the lowest level of the liquid, the opening must be above a horizontal plane at the level of the liquid inlet opening of the downcomer. These two planes are illustrated as horizontal planes A and B respectively in FIG. 4. These planes are perpendicular to the lower leg of the liquid-transfer conduit.

The invention may therefore be characterized as a fractionation tray downcomer which comprises in cooperative combination: a liquid-transfer conduit defining an enclosed liquid flow path, the liquid-transfer conduit having an upper portion with the shape of an inverted U located in an upper first half of the liquid-transfer conduit, the upper portion having a horizontal section which divides the liquid-transfer conduit into a shorter first leg and a longer second leg, the liquid-transfer conduit having a first opening located in the first leg and a second opening located in the second leg; and a curved siphon-breaking vapor conduit defining an enclosed vapor flow path, the siphon-breaking conduit being joined to the upper portion of the liquid-transfer conduit and operably communicating with the liquid flow path, the siphon-breaking conduit passing downward through a first plane perpendicular to the second leg of the liquid-transfer conduit and passing through an outer surface of the horizontal section of the upper portion of the liquid-transfer conduit which is closest to the second opening, the siphon-breaking conduit having a third opening located between the first plane and a second plane perpendicular to the second leg of the liquid-transfer conduit and passing through the first opening in the first leg of the liquid-transfer conduit.

The feed to the top tray may be pulsed to induce the pulsing action and control the magnitude of the pulses as previously described. Alternatively, the feed to the top tray may be constant and the top tray may generate the initial pulses. The elements of the top tray are then sized to control the magnitude and interval between the pulses. The optimum residence time for each pulse is dependent on the time required for the liquid to approach a preselected degree of equilibrium with the rising vapors. The time required to fill the liquid inventory of the top tray between the levels at which the siphon is initiated and terminated sets the time between pulses and the residence times of the lower trays. The main feed to the top tray is the reflux stream, and this is normally at an approximately steady rate. There will be some addition to the quantity of liquid on the tray by condensation of rising vapors and also some loss due to vaporization. The smaller rate of this constant input must be taken into consideration and in sizing the distance between the top of the weir and the end of the siphon-breaking conduit. With a constant feed rate, this distance will be greater than on the lower trays since the volume of liquid removed by the pulsing action is not replaced by a similar pulse as on the lower trays.

The downcomers should be sized for relatively rapid transfer of the pulses to allow an adequate residence time without reducing column capacity. The capacity of the liquid-transferring conduit used on each tray should be equal to that used in the next lower tray. This capacity is affected by the composition of the liquid. If the conduit has a smaller capacity, then it is possible that the siphon effect will be prematurely broken on the tray below. If it has a greater capacity, then the liquid level on the next lower tray will be raised until the downcomer can reduce it. This would reduce the rate of vapor flow through the upper tray and disturb both the temperature and vapor production of the upper tray. Since a major variation in the liquid level of the top tray will also cause a disturbance in the column's overhead vapor, it may be preferred that the reflux stream is pulsed and that the top tray is identical to the others used in the column. The reflux stream may be pulsed by an apparatus using a siphon action as on the trays or by a periodically operated valve means.

Other modifications of the apparatus described herein will become apparent to those skilled in the art. Such variation is not intended to be excluded by its lack of description. For instance, the upper internal surface of the preferred dome-like capping plate may have an inverted cone attached to it to limit cavitation of the downflowing liquid. The trays may be constructed with a plurality of downcomers or with downcomers of different cross-sections or placed in different locations. If more than one downcomer is used, the siphon-breaking conduit may be branched to communicate with the liquid flow path within each and thereby break the siphon in each downcomer simultaneously. Further, the tray may be divided into a plurality of different vapor-liquid contacting sections by vertical weirs crisscrossing the surface of the tray. This allows the use of several small pulses between the respective sections of contiguous trays. The construction of the individual trays within the column may vary. For instance, only alternate trays may be sectioned or different types of vapor-liquid contacting means may be placed on the surface of the tray. The interval between pulses and/or the quantity of the pulse may be designed differently in different parts of the column to coincide with differing operating conditions. This would be especially true for those trays used below an intermediate feed point as compared to those used above.

We claim as our invention:

1. In combination with a fractionation tray a fractionation tray downcomer which comprises in cooperative combination:
   a. a liquid-transfer conduit defining an enclosed liquid flow path, the liquid-transfer conduit having an upper portion with the shape of an inverted U located in an upper first half of the liquid-transfer conduit, the upper portion having a horizontal section which divides the liquid-transfer conduit into a shorter first leg and a longer second leg, the liquid-transfer conduit having a first opening located in the first leg and a second opening located in the second leg; and,
   b. a curved, siphon-breaking vapor conduit defining an enclosed vapor flow path, the siphon-breaking conduit being joined to the upper portion of the liquid-transfer conduit and operably communicating with the liquid flow path, the siphon-breaking conduit passing downward through a first plane perpendicular to the second leg of the liquid-transfer conduit and passing through an outer surface of the horizontal section of the upper portion of the liquid-transfer conduit which is closest to said second opening in said second leg of said liquid-transfer conduit, said siphon-breaking conduit having an opening located between the first plane and a second plane perpendicular to the second leg of the liquid-transfer conduit and passing through said first opening in the first leg of said liquid-transfer conduit, whereby liquid is transferred from said fractionation tray in a periodic pulse-like manner, said periodic transfer commencing when the liquid level on said fractionation tray initiates siphonic flow through said liquid-transfer conduit, said liquid flow being terminated when the liquid level on said fractionation tray descends to said opening of said siphon-breaking conduit and vapor flow is initiated in said siphon-breaking conduit.

2. The downcomer of claim 1 further characterized in that there is provided a substantially straight vapor venting conduit which passes through a wall of the second leg of the liquid-transfer conduit and extends into the liquid-transfer conduit and through the second plane, said vapor venting conduit being positioned to form an annulus within the liquid-transfer conduit.

* * * * *